(12) United States Patent
Chang et al.

US007335795B2

(10) Patent No.: US 7,335,795 B2
(45) Date of Patent: Feb. 26, 2008

(54) CROSSLINKED AMINE POLYMERS

(75) Inventors: Han Ting Chang, Livermore, CA (US);
Dominique Charmot, Campbell, CA
(US); Eric Connor, Los Gatos, CA
(US); Florence Roger, Santa Clara, CA
(US)

(73) Assignee: Ilypsa, Inc., Santa Clara, CA (US)

( * ) Notice: Subject to any disclaimer, the term of this patent is extended or adjusted under 35 U.S.C. 154(b) by 134 days.

(21) Appl. No.: 10/806,495

(22) Filed: Mar. 22, 2004

(65) Prior Publication Data

US 2005/0209423 A1    Sep. 22, 2005

(51) Int. Cl.
*C07C 211/11* (2006.01)
(52) U.S. Cl. .................. 564/511; 564/512; 514/772.3; 525/526
(58) Field of Classification Search ............. 514/772.3; 564/511, 512; 525/526
See application file for complete search history.

(56) References Cited

U.S. PATENT DOCUMENTS

| | | | |
|---|---|---|---|
| 3,308,020 A | 3/1967 | Wolf et al. | |
| 3,499,960 A | 3/1970 | Macek et al. | |
| 3,692,895 A | 9/1972 | Nelson et al. | |
| 3,930,810 A * | 1/1976 | Gattuso | 44/332 |
| 3,974,272 A | 8/1976 | Polli et al. | |
| 4,015,939 A | 4/1977 | Lewin et al. | |
| 4,027,009 A | 5/1977 | Grier et al. | |
| 4,075,177 A | 2/1978 | Bonnet et al. | |
| 4,135,880 A | 1/1979 | Mangiardi et al. | |
| 4,410,688 A | 10/1983 | Denkewalter et al. | |
| 4,507,466 A | 3/1985 | Tomalia et al. | |
| 4,558,120 A | 12/1985 | Tomalia et al. | |
| 4,568,737 A | 2/1986 | Tomalia et al. | |
| 4,587,329 A | 5/1986 | Tomalia et al. | |
| 4,599,400 A | 7/1986 | Tomalia et al. | |
| 4,605,701 A | 8/1986 | Harada et al. | |
| 4,631,337 A | 12/1986 | Tomalia et al. | |
| 4,690,985 A | 9/1987 | Tomalia et al. | |
| 4,734,200 A | 3/1988 | Berry | |
| 4,737,550 A | 4/1988 | Tomalia | |
| 4,747,881 A | 5/1988 | Shaw et al. | |
| 4,902,501 A | 2/1990 | Bandi et al. | |
| 5,091,175 A | 2/1992 | Imondi et al. | |
| 5,254,669 A | 10/1993 | Blackborow | |
| 5,338,532 A | 8/1994 | Tomalia et al. | |
| 5,380,522 A | 1/1995 | Day | |
| 5,447,726 A | 9/1995 | Nomura | |
| 5,451,397 A | 9/1995 | Albright et al. | |
| 5,487,888 A | 1/1996 | Mandeville, III et al. | |
| 5,496,545 A | 3/1996 | Holmes-Farley et al. | |
| 5,530,092 A | 6/1996 | Meijer et al. | |
| 5,607,669 A | 3/1997 | Mandeville, III et al. | |
| 5,618,530 A | 4/1997 | Mandeville, III et al. | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,698,662 A | 12/1997 | Stoelwinder et al. | |
| 5,702,696 A | 12/1997 | Mandeville, III et al. | |
| 5,968,499 A | 10/1999 | Hider et al. | |
| 5,980,881 A | 11/1999 | Mitsuka et al. | |
| 5,985,938 A | 11/1999 | Holmes-Farley et al. | |
| 6,007,803 A | 12/1999 | Mandeville, III et al. | |
| 6,034,129 A | 3/2000 | Mandeville, III et al. | |
| 6,060,604 A | 5/2000 | Yang et al. | |
| 6,129,910 A | 10/2000 | Holmes-Farley et al. | |
| 6,132,706 A | 10/2000 | Hider et al. | |
| 6,180,094 B1 | 1/2001 | Sasaki et al. | |
| 6,180,754 B1 | 1/2001 | Stutts et al. | |
| 6,281,252 B1 | 8/2001 | Holmes-Farley et al. | |
| 6,333,051 B1 | 12/2001 | Kabanov et al. | |
| 6,361,768 B1 | 3/2002 | Galleguillos et al. | |
| 6,362,266 B1 | 3/2002 | Buchholz et al. | |
| 6,383,518 B1 | 5/2002 | Matsuda et al. | |
| 6,423,754 B1 | 7/2002 | Holmes-Farley et al. | |
| 6,471,968 B1 | 10/2002 | Baker, Jr. et al. | |
| 6,475,510 B1 | 11/2002 | Venkatesh et al. | |
| 6,509,013 B1 | 1/2003 | Holmes-Farley et al. | |
| 6,566,407 B2 | 5/2003 | Holmes-Farley et al. | |
| 6,593,366 B2 | 7/2003 | Mandeville, III et al. | |
| 6,646,083 B2 | 11/2003 | Hirano et al. | |
| 6,696,087 B2 | 2/2004 | Matsuda et al. | |

(Continued)

FOREIGN PATENT DOCUMENTS

| | | |
|---|---|---|
| DE | 10305807 A1 | 8/2004 |
| EP | 0575596 B1 | 12/1993 |
| EP | 0373852 B1 | 10/1994 |
| EP | 0672703 A1 | 9/1995 |
| EP | 0707611 B1 | 4/1996 |
| EP | 0741756 B1 | 11/1996 |
| EP | 0997148 B1 | 5/2000 |
| EP | 0793960 B1 | 8/2001 |
| EP | 1153940 A1 | 11/2001 |
| EP | 1209146 B1 | 5/2002 |

(Continued)

OTHER PUBLICATIONS

Brezina, B. et al., "Acid loading during treatment with sevelamer hydrochloride: mechanisms and clinical implications". *Kidney International*, (2004), 66:S39-S45.

(Continued)

*Primary Examiner*—Robert D. Harlan
(74) *Attorney, Agent, or Firm*—Senniger Powers

(57) ABSTRACT

The present invention provides methods and compositions for the treatment of ion imbalances. In particular, the invention provides polymeric and pharmaceutical compositions comprising crosslinked amine polymers. Methods of use of the polymeric and pharmaceutical compositions for therapeutic and/or prophylactic benefits are disclosed herein. Examples of these methods include the treatment of renal diseases and hyperphosphatemia.

68 Claims, No Drawings

U.S. PATENT DOCUMENTS

| | | |
|---|---|---|
| 6,726,905 B1 | 4/2004 | Mandeville, III et al. |
| 6,733,780 B1 | 5/2004 | Tyler et al. |
| 6,767,549 B2 | 7/2004 | Mandeville, III et al. |
| 2002/0028887 A1 | 3/2002 | Hirano et al. |
| 2002/0034723 A1 | 3/2002 | Leinenbach et al. |
| 2002/0054903 A1 | 5/2002 | Tyler et al. |
| 2002/0064511 A1 | 5/2002 | Simon et al. |
| 2002/0146386 A1 | 10/2002 | Simon et al. |
| 2002/0168333 A1 | 11/2002 | Burke |
| 2002/0182168 A1 | 12/2002 | Holmes-Farley |
| 2002/0187120 A1 | 12/2002 | Holmes-Farley et al. |
| 2002/0187121 A1 | 12/2002 | Burke |
| 2003/0039627 A1 | 2/2003 | Homes-Farley et al. |
| 2003/0049226 A1 | 3/2003 | Burke et al. |
| 2003/0078366 A1 | 4/2003 | McDonnell et al. |
| 2003/0091530 A1 | 5/2003 | Goto et al. |
| 2003/0092782 A1 | 5/2003 | Goto et al. |
| 2004/0018169 A1 | 1/2004 | Holmes-Farley et al. |
| 2004/0059065 A1 | 3/2004 | Goto et al. |
| 2004/0120922 A1 | 6/2004 | Burke |
| 2004/0170600 A1 | 9/2004 | Simon et al. |
| 2004/0194334 A1 | 10/2004 | Rea |
| 2005/0096438 A1 | 5/2005 | Chang et al. |
| 2005/0131138 A1 | 6/2005 | Connor et al. |
| 2005/0147580 A1 | 7/2005 | Connor et al. |
| 2005/0165190 A1 | 7/2005 | Chang et al. |
| 2005/0239901 A1 | 10/2005 | Chang et al. |
| 2005/0276781 A1 | 12/2005 | Ross et al. |

FOREIGN PATENT DOCUMENTS

| | | |
|---|---|---|
| EP | 1283046 A1 | 2/2003 |
| EP | 1304104 A2 | 4/2003 |
| JP | 1998059851 A | 3/1998 |
| JP | 1998130154 A | 5/1998 |
| JP | 2003155429 | 5/2003 |
| WO | WO82/00257 | 2/1982 |
| WO | WO93/14147 A1 | 7/1993 |
| WO | 94019379 | 9/1994 |
| WO | WO94/27619 A1 | 12/1994 |
| WO | WO95/02008 A1 | 1/1995 |
| WO | WO95/05184 A1 | 2/1995 |
| WO | WO95/19384 A1 | 7/1995 |
| WO | WO95/20619 A1 | 8/1995 |
| WO | WO97/23514 A1 | 7/1997 |
| WO | WO97/49736 A2 | 12/1997 |
| WO | WO98/17707 A1 | 4/1998 |
| WO | WO98/42355 A1 | 10/1998 |
| WO | WO99/14297 A1 | 3/1999 |
| WO | WO99/40990 A1 | 8/1999 |
| WO | WO 01/28527 A2 | 4/2001 |
| WO | WO 01/38423 A1 | 5/2001 |
| WO | WO 02/32974 A2 | 4/2002 |
| WO | WO 02/032974 A3 | 4/2002 |
| WO | WO 02/077074 A1 | 10/2002 |
| WO | WO 2004/037274 A1 | 5/2004 |
| WO | WO 2005/065291 A2 | 7/2005 |
| WO | WO 2006/040579 A1 | 4/2006 |

OTHER PUBLICATIONS

Chang, H.T. et al., U.S. Appl. No. 10/701,385 entitled "Polyamine polymers", filed Nov. 3, 2003.

Chertow, G.M. et al. "Long-term effects of sevelamer hydorchloride on the calcium x phosphate product nad lipid profile of haemodialysis patients". *Nephrology Dialysis Transplantation*, (1994), 14:2907-2914.

Hagmaier, V. et al., "Test of efficacy of an oxalate-binding anion exchanger Colestid in healthy subjects for use in idiopathic calcium-oxalate urolithiasis". *Helveica Chirurgica Acta*, (Aug. 1981), 48(3-4):421-424.

Ross, E.A. et al., "Synthesis of molecularly imprinted polymers (MIPs) for phosphate binding". Published in the abstract list of Renal Week Conference (Sep. 20, 2004), ASN.

Slatopolsky, E.A. et al., "RenaGel®, a nonabsorbed calcium-and aluminum-free phosphate binder, lowers serum phosphorus and parathyroid hormone". *Kidney International*, (1999), 55:299-307.

Klapper, M. et al., "Poly(methylene amine): A Polymer with the Maximum Possible Number of Amino Groups on a Polymer Backbone", *Angew. Chem. Int. Ed.*, vol. 42 (2003), pp. 4687-4690.

Zimmer, A. et al., "Ligand Synthesis and Metal Complex Formation of 1,2,3-Triaminopropane", *Eur. J. Inorg. Chem.*, Jul. 1998, pp. 2079-2086.

Reiss, Guido J. et al. 2000. Protonation products of pentaaminopentane as novel building blocks for hydrogen-bonded networks. *Acta Crysta*. C56: 284-288.

Zimmer, Anja et al. 2001. Complex Formation of $Ni^{II}$, $Cu^{II}$, $Pd^{II}$, and $Co^{III}$ with 1,2,3,4-Tetraaminobutane. *Chem. Eur. J.* 7(4):917-931.

Barsotti, G. et al. 1979. Anion-Exchange Resins for the Uremic Hyperphosphatemia. *Mineral and Electrolyte Metabolism*. 2(1):206.

Buhleier, Egon et al. 1978. "Cascade"- and "Nonskid-Chain-like" Syntheses of Molecular Cavity Topologies. *Syntheses*. 1978(02):155-158.

Burke, Steven K. 2000. Renagel®: reducing serum phophorus in haemodialysis patients. *Hospital Medicine*. 61(9): 622-627.

Burt, Helen M. et al. 1985-86. In Vitro Studies Using Ion Exchange Resins as Potential Phosphate Binders for Renal Failure Patients. *Uremia Investigation*.9(1):35-44.

Burt, Helen. M. et al. 1986. Ion-Exchange Resins as Potential Phosphate-Binding Agents for Renal Failure Patients: Effect of the Physicochemical Properties of Resins on Phosphate and Bile Salt Binding. *Journal of Pharmaceutical Sciences*. 76(5):379-383.

Cholestyramine. 1998. Cholestyramine for oral suspension. Copley Pharmaceutical, Inc. Canton, MA. (Package Insert).

Colestid®. 2003. Colestid® micronized colestipol hydrochloride tablets. Pharmacia & Upjohn Company, Kalamazoo, MI. (Package Insert).

Coli, L. et al. 1992. Phosphate Removal by Resin Hemoperfusion Efficacy and Biocompatibility of a New Exchange Resin. *Biomaterials, Artificial Cells, and Immobilization Biotechnology*. 20(5): 1153-1163.

De Simone, Renato et al. 1978. New Microporous Cholestyramine Analog for Treatment of Hypercholesterolemia. *Journal of Pharmaceutical Sciences*. 67(12): 1695-1698.

Grynpas, R. et al. 1986. Organic ion exchange resins as substitutes for aluminum hydroxide gels. *Life Support Systems*.4(Suppl. 2): 276-8.

Hagmaier, V. et al. 1981. Investigation of the efficacy of oxalate-binding anionic exchanger Colestid in healthy subjects for use in idiopathic calcium-oxalate-urolithiasis. *Helv. Chir.Acta*. 48(3/4): 421-424.

Hardy, P. et al. 1998. Inhibition of Gastric Secretion by Omeprazole and Efficiency of Calcium Carbonate on the Control of Hyperphosphatermia in Patients on Chronic Hemodialysis. *Artificial Organs*. 22(7): 569-573.

Honda, Yoshiteru et al. 2000. Studies on Adsorption Characteristics of Bile Acids and Methotrexate to a New Type of Anion-Exchange Resin, Colestimide. *Chem. Pharm. Bull*. 48(7): 978-981.

Hurst, P.E. et al. 1963. The Effect of Oral Anion Exchange Resins on FÆCAL Anions. Comparison with Calcium Salts and Aluminum Hydroxide. *Clin. Sci.* 24: 187-200.

Konechnik, Thomas J. et al. 1989. In Vitro Adsorption of Bile Salts by Colestipol Hydrochloride. *Pharmaceutical Research*. 6(7): 619-623.

Kurihara, Satoshi et al. 2005. Effect of MCI-196 (colestilan) as a phophate binder on hyperphosphataemia in haemodialysis patients: a double-blind, placebo-controlled, short-term trial. *Nephrol Dial Tranplant*. 20(2): 424-430.

McGary, T.J. et al. 1984-85. Polycation as an Alternative Osmotic Agent and Phophate Binder in Peritoneal Dialysis. *Uremia Investigation*. 8(2): 79-84.

Nolan, James P. et al. 1975. Endotoxin Binding by Charged and Uncharged Resins. *Proceedings of the Society for Experimental Biology and Medicine.* 149: 766-770.

Peppas, Nicholas A. et al. 1993. Dendrimers and Star Polymers for Pharmaceutical and Medical Applications. *Proceed. Intern. Symp. Control. Rel. Bioact. Mater.* 20: 143-144.

Schneider, H. et al. 1984. Aluminum-free oral phosphate binder. *Dep. Nephrol. Hypertension.* 1(2): 76-9. (Abstract Only).

Sechet, A. et al. 1999. Inhibition de la secretion gastrique par l'omeprazole et efficacite du carbonate de calcium sur le controle de l'hyperphosphoremie des patients hemodialyses chroniques [Inhibition of gastric secretion by omeprazole and efficacy of calcium carbonate in the control fo hyperphosphatermia in patients on maintenance hemodialysis]. *Nephrologie.* 20(4): 213-216. (Article in French with English Summary).

Shataeva L.K. et al. 1982. [Effect of FAF anionite swelling on its sorption properties]. *Prikl Biokhim Microbiol.* 18(1): 65-70. (in Russian w/ English abstract).

Swearingen, Ronald A. et al. 2002. Determination of the binding parameter constants of Renagel® capsules and tablets utilizing the Langmuir approximation at various pH by ion chromatography. *Journal of Pharmaceutical and Biomedical Analysis.* 29: 195-201.

WelChol® Tablets. Licensed from: GelTex Pharmaceuticals, Inc. (Package Insert).

Wrong, O.M. 1972. Aluminum Toxicity. *Lancet.* 2(7772): 334-5.

Wrong, O.M. 1973. Anion-Exchange Resins in Treatment of Uræmic Acidosis and Hyperphosphatæmia. *Lancet.* 1(7801):493.

Daniel, Marie-Christine, et al. 2003. Supramolecular H-Bonded Assemblies of Redox-Active Metallodendrimers and Positive and Unusual Dendritic Effects on the Recognition of H2PO4. *J. Am. Chem., Soc.* 125(5): 1150-1151.

Kioussis, Dimitri R., et al. 2005. Characterization of anion diffusion in polymer hydrogels used for wastewater remediation. *Polymer.* 46: 9342-9347.

Kioussis, Dimitri R., et al. 2005. Characterization of network morphology in anion binding hydrogels used for wastewater remediation. *Polymer.* 46: 10167-10172.

Mazzeo, Jeffrey R., et al. 1999. A phosphate binding assay for sevelamer hydrochloride by ion chromatography. *J. Pharm. Biomed. Anal.* 19: 911-915.

Panova, T.V., et al. 2004. Interaction of Poly(propylenimine) Dendrimers with Polyanionic Hydrogels. *Faculty of Chemistry, Moscow State University.* 46(5): 783-798. (in Russian with English Abstract).

Tiitu, Mari, et al. 2005. Aminic epoxy resin hardeners as reactive solvents for conjugated polymers; polyaniline base/epoxy composites for anticorrosion coatings. *Polymer.* 46: 6855-6861.

Bilicki, C.V., et al., Effect of Anions on Adsorption of Bile Salts by Colestipol Hydrochloride, Pharmaceutical Research, 1989, pp. 794-797, vol. 6, No. 9, Plenum Publishing Corporation.

Bleyer, A.J., et al., A Comparison of the Calcium-Free Phosphate Binder Sevelamer Hydrochloride With Calcium Acetate in the Treatment of Hyperphosphatemia in Hemodialysis Patients, American Journal of Kidney Diseases, 1999, pp. 694-701, vol. 33, No. 4, National Kidney Foundation, Inc.

Covassin, L., et al., Synthesis of Spermidine and Norspermidine Dimers as High Affinity Polyamine Transport Inhibitors, Bioorganic & Medicinal Chemistry Letters, 1999, vol. 9, pp. 1709-1714, Elsevier Science Ltd.

Jansen, Bart A.J., et al., A Tetranuclear Platinum Compound Designed to Overcome Cisplatin Resistance, Eur. J. Inorg. Chem., 1999, pp. 1429-1433, WILEY-VCH Verlag GmbH, D-69451 Weinheim.

Malluche, H.H., et al., Management of hyperphosphataemia of chronic kidney disease: lessons from the past and future directions, Nephrol Dial Transplant, 2002, pp. 1170-1175, vol. 17, European Renal Association-European Dialysis and Transplant Association.

Rauter, H., et al., Selective Platination of Biologically Relevant Polyamines. Linear Coordinating Spermidine and Spermine as Amplifying Linkers in Dinuclear Platinum Complexes, Inorg. Chem., 1997, pp. 3919-3927, vol. 36, American Chemical Society.

Sugano, M., et al., A novel use of chitosan as a hypocholesterolemic agent in rats, The American Journal of Clinical Nutrition, 1980, pp. 787-793, vol. 33.

* cited by examiner

CROSSLINKED AMINE POLYMERS

BACKGROUND OF THE INVENTION

In patients with normal kidney function, calcium and phosphorus balance is maintained through the interaction of parathyroid hormone (PTH) and calcitriol, an active metabolite of vitamin D. PTH provides a mechanism for controlling extracellular calcium and phosphate concentrations by regulating intestinal reabsorption, renal excretion, and exchange of these ions between the extracellular fluid and bone.

With progressive renal insufficiency, however, there is increased phosphorus retention by the failing kidney. In order to restore phosphorus balance, compensatory elevation in PTH levels is triggered, which increases renal resorption of calcium, while decreasing tubular resorption of phosphorus. The net effect of compensatory hyperparathyroidism in this early stage of renal disease is that serum phosphorus levels are maintained within the normal range.

The retention of phosphorus as a result of the decreased ability of the diseased kidney to excrete the filtered phosphate leads to a decrease in serum free calcium, which in turn stimulates the secretion of more PTH. With each progressive reduction in kidney function, a new steady state is achieved in which serum phosphate is restored to normal at the expense of a sustained high level of PTH. The cycle is repeated as renal function declines until sustained and severe hyperparathyroidism is present; eventually the compensatory mechanism is not able to control the increasing serum phosphorus levels. Once the glomerular filtration rate has decreased to <20% of normal, overt hyperphosphatemia becomes evident. In end-stage renal disease patients (where the compensatory mechanism mediated by PTH is no longer effective), the increase in plasma phosphate results not only from decreased excretion but also from continual high levels of PTH, which further exacerbates the problem by releasing calcium and phosphate from the bone.

The clinical manifestations of hyperphosphatemia are varied and have considerable mortality risks. Severe hyperphosphatemia can induce hypocalcemia, which aggravates the imbalance in PTH levels further by increasing the production of this hormone. Hyperphosphatemia inhibits renal synthesis of calcitriol, which causes an exacerbation of the hypocalcemia condition. The occurrence of severe hypocalcemia with tetany and ectopic calcifications is the most severe manifestation of hyperphosphatemia. Calcification may occur in the joints, soft tissues, lungs, kidney, and conjunctiva. Soft tissue calcification has been linked to cardiovascular risk, and cardiovascular disease is the cause of death in more than 45% of all dialysis patients. Renal osteodystrophy with effects on the bones and muscles is common in end stage renal disease (ESRD) patients, as well as severe pruritis. The high PTH level associated with developing and severe renal disease has indirect actions on the central and peripheral nervous system, and the myocardial tissues, creating further disorders such as hyperlipemia, muscle growth retardation, arteriosclerosis, bone loss, and immunodeficiency.

Prevention and treatment of hyperphosphatemia is achieved by a variety of means, including dietary control of phosphorus intake, dialysis and oral phosphate binders. Dialysis, however, does not remove phosphate ions well from the serum because of the slow equilibrium between intracellular and extracellular phosphorus. The treatments of choice focus instead on a phosphorus controlled diet and the administration of phosphate binders taken at meals. A low phosphorus diet is not a long-term option, however, since patient compliance is difficult and the daily dietary phosphorus intake cannot be lowered below ~1000 mg/day, without restricting protein intake even further than the 1.2 g/kg/day of protein recommended for hemodialysis patients.

Oral phosphate binders comprise two main classes: inorganic metal salts and polymer resins, often referred to as metal-free binders. Examples of the former category include compounds such as aluminum carbonate, calcium carbonate, calcium acetate (PhosLo), and lanthanum carbonate (Fosrenol). While aluminum and calcium salts have been the treatment of choice for years, they produce soluble metal ions that cross the gastrointestinal membrane and enter the blood stream, producing toxic effects. For instance, aluminum carbonate salts have been shown to be involved in cases of encephalopathy and aluminum osteopathy due to aluminum bone absorption. Calcium binders also generate large amounts of soluble calcium cations, the absorption of which can cause hypercalcemia. Further, although the causative effect is not fully demonstrated, high calcium x phosphate product has been held responsible for soft tissue calcification and cardiovascular disease. Lanthanum carbonate seems to produce less metal absorption, but bone accumulation of lanthanum has been established and the long-term effect of such accumulation in humans is still unclear.

Metal free binders include ion exchange resins and crosslinked polyallylamine resins. Ion exchange resins include cholestyramine, colestipol hydrochloride, and Dowex. These resins have been proposed as an alternative to metal salts, but their low capacity and their lack of palatability have precluded their wide use in the clinic. Crosslinked polyallylamine, like sevelamer hydrochloride (Renagel), was introduced as the next generation of metal-free phosphate binder resins. However, the phase 1 clinical trials performed on healthy volunteers indicate that the in vivo binding capacity of Renagel is much lower than anticipated from in vitro studies. As a consequence ESRD patients still need a high dosage of Renagel to meet clinical endpoints, leading to adverse effect such as gastrointestinal discomfort and problems with patient compliance.

Accordingly, there is a need to develop better phosphate binding therapies, with reduced side effects for patients with hyperphosphatemia.

BRIEF SUMMARY OF THE INVENTION

In one aspect, the present invention relates to polymeric compositions comprising crosslinked amine moieties. In a first embodiment the invention is a crosslinked amine polymer comprising an amine of formula I

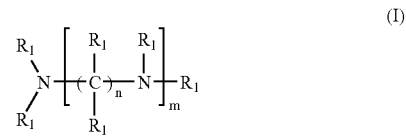

wherein each n, independently, is equal to or greater than 3; m is equal to or greater than 1; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

A second embodiment of the invention is a crosslinked amine polymer comprising an amine of formula II

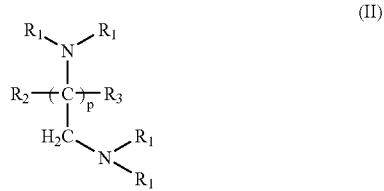

(II)

wherein p is 1, 2, 3, or 4; each $R_1$, independently, is H or optionally substituted alkyl or aryl or is linked to a neighboring $R_1$ to form an optionally substituted alicyclic, aromatic, or heterocyclic group; $R_2$ and $R_3$, each independently, are H or optionally substituted alkyl or aryl, with the proviso that when p=1, both $R_2$ and $R_3$ are not H and when p=2, 3, or 4, $R_2$ and $R_3$ are H, alkyl or —C($R_1$)$_2$—$R_4$—N($R_1$)$_2$, $R_4$ being either a bond or methylene; and the amine is crosslinked with a crosslinking agent.

A third embodiment of the invention is a crosslinked amine polymer comprising an amine of formula III

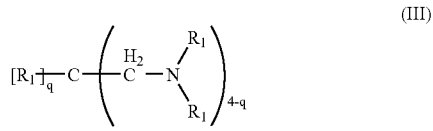

(III)

wherein q is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

A fourth embodiment of the invention is a crosslinked amine polymer comprising an amine of formula IV

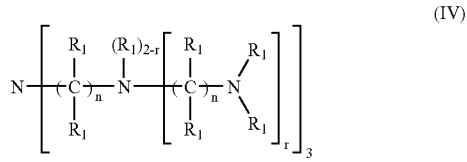

(IV)

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

A fifth embodiment of the invention is a crosslinked amine polymer comprising an amine of formula V

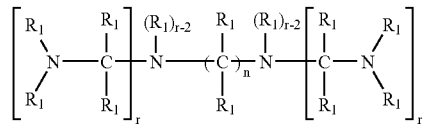

(V)

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

In another aspect, the invention provides methods of treating an animal, including a human. The method generally involves administering an effective amount of a crosslinked amine polymer described herein.

Another aspect of the invention is a pharmaceutical composition comprising one or more polymers of the present invention with at least one pharmaceutically acceptable carrier. The polymers described herein have several therapeutic applications. For example, the crosslinked amine polymers are useful in removing phosphate, from the gastrointestinal tract. In some embodiments, the crosslinked amine polymers are used in the treatment of phosphate imbalance disorders and renal diseases.

In yet another aspect, the crosslinked amine polymers are useful for removing other anionic solutes, such as chloride, bicarbonate, and/or oxalate ions. Polymers removing oxalate ions find use in the treatment of oxalate imbalance disorders. Polymers removing chloride ions find use in treating acidosis, for example. In some embodiments, the crosslinked amine polymers are useful for removing bile acids and related compounds.

DETAILED DESCRIPTION OF THE INVENTION

Crosslinked Amine Polymers

In one aspect, the present invention provides methods of using compositions comprising a polymer that contains crosslinked amine moieties. Polymers, including homopolymers and copolymers, with repeating crosslinked amine units are referred to herein as crosslinked amine polymers. The repeating amine units in the polymer can be separated by the same or varying lengths of repeating linker (or intervening) units. In some embodiments, the polymers comprise of repeat units of an amine plus intervening linker unit. In other embodiments, multiple amine units are separated by one or more linker units.

In a first embodiment the invention is a method for removing phosphate from the gastrointestinal tract of an animal by administering an effective amount of a crosslinked amine polymer, wherein said polymer comprises an amine of formula I

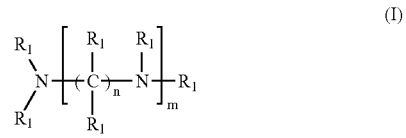

(I)

wherein each n, independently, is equal to or greater than 3; m is equal to or greater than 1; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

Preferred amines of formula I include:

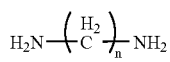

n: 3, 4, or 5

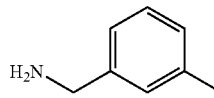 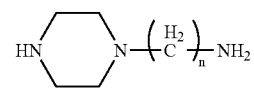

A second embodiment of the invention is a method of removing phosphate from the gastrointestinal tract of an animal subject by administering an effective amount of a crosslinked amine polymer, wherein said polymer comprises an amine of formula II

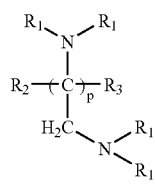

(II)

Wherein p is 1, 2, 3, or 4; each $R_1$, independently, is H or optionally substituted alkyl or aryl or is linked to a neighboring $R_1$ to form an optionally substituted alicyclic, aromatic, or heterocyclic group; $R_2$ and $R_3$, each independently, are H or optionally substituted alkyl or aryl, with the proviso that when p=1, both $R_2$ and $R_3$ are not H and when p=2, 3, or 4, $R_2$ and $R_3$ are H, alkyl or —C($R_1$)$_2$—$R_4$—N($R_1$)$_2$, $R_4$ being either a bond or methylene; and the amine is crosslinked with a crosslinking agent.

Preferred amines of formula II include:

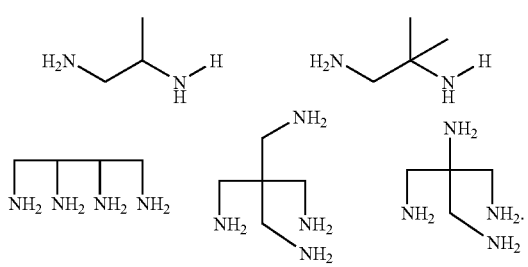

A third embodiment of the invention is a method of removing phosphate from the gastrointestinal tract of an animal by administering an effective amount of a crosslinked amine polymer, wherein said polymer comprises an amine of formula III

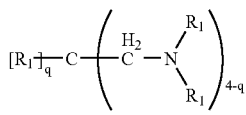

(III)

wherein q is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

Preferred amines of formula III include:

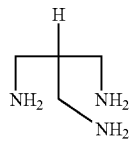 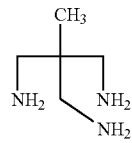

A fourth embodiment of the invention is a method of removing phosphate from the gastrointestinal tract of an animal by administering an effective amount of a crosslinked amine polymer, wherein said polymer comprises an amine of formula IV

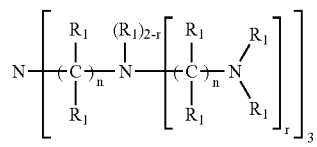

(IV)

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

A preferred amine of formula IV includes:

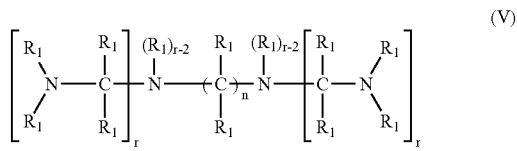

A fifth embodiment of the invention is a method of removing phosphate from the gastrointestinal tract of an animal by administering an effective amount of a crosslinked amine polymer, wherein said polymer comprises an amine of formula V (V)

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent.

Preferred amines of formula V include:

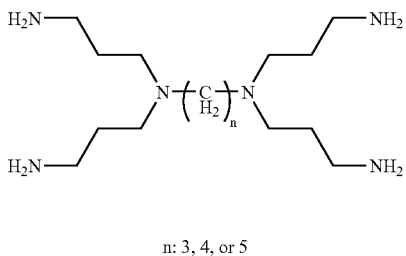

n: 3, 4, or 5

In another aspect, the present invention provides compositions comprising a polymer that contains crosslinked amine moieties. These polymers, including homopolymers and copolymers, comprise of repeating crosslinked amine units.

In a first embodiment the invention is a crosslinked amine polymer, wherein said polymer comprises an amine of formula I as described above. A second embodiment of the invention is a crosslinked amine polymer, wherein said polymer comprises an amine of formula II as described above. A third embodiment of the invention is a crosslinked amine polymer, wherein said polymer comprises an amine of formula III as described above. A fourth embodiment of the invention is a crosslinked amine polymer, wherein said polymer comprises an amine of formula IV as described above. A fifth embodiment of the invention is a crosslinked amine polymer, wherein said polymer comprises an amine of formula V as described above.

The polymers comprising of an amine of Formula II have been described above with p=1-4. In addition, in some of the embodiments, the amines of Formula II include amines wherein p is greater than 4. In various embodiments, p can be more than 8, more than 12, more than 16, or more than 20. In other embodiments, p can be less than 25, less than 20, less than 15, or less than 10.

The amines represented by general formulas I-VI can be synthesized by methods well known in the art. These synthesis techniques include catalytic conversion from alcohols, reductive amination of carbonyl compounds, Michael additions, and hydrogenation of nitriles (see, for example, Karsten Eller et al, Ullmann's Encyclopedia of Industrial Chemistry 2002 by Wiley-VCH Verlag GmbH & Co. KGaA). Several small amine monomers and/or amine plus intervening linker units are also commercially available.

In one embodiment, an amine useful in the present invention, tetramethylene tetramine, depicted below, is synthesized by catalytic hydrogenation of the commercially available diaminomaleonitrile (DAMN):

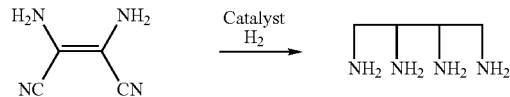

Polymerization can be achieved by methods known to those in the art, examples of which are illustrated in detail in the Examples disclosed herein. For example, the crosslinking reaction is carried out either in solution of bulk (i.e. using the neat amine and neat crosslinker compounds) or in dispersed media. When a bulk process is used, solvents are selected so that they co-dissolve the reactants and do not interfere with the amine crosslinking reaction. Suitable solvents include water, low boiling alcohols (methanol, ethanol, butanol), dimethylformamide, dimethylsulfoxide, acetone, methylethylketone, and the like.

Processes in dispersed media, include inverse suspension, direct suspension and aerosols, and the like. The continuous phase can be selected from apolar solvents such as toluene, benzene, hydrocarbon, halogenated solvents, supercritical carbon dioxide, and the like. With a direct suspension process, water can be used, although salt brines are also useful to "salt out" the amine and crosslinker reagents in a droplet separate phase, as described in U.S. Pat. No. 5,414,068.

The crosslinker to amine mole ratios control the extent of gel material formed as well as its crosslinking density. Too low a ratio may lead to incomplete crosslinking and formation of soluble oligomers, while too high a ratio may produce extremely tight network with little binding properties. The amine component can be either one or a combination of several amines, and the same applies to the crosslinker component. Optimization may be required for any new combination of amines and crosslinkers, since the functionality of either can influence the extent of gel formation and swelling characteristics. In some embodiments, crosslinker to amine molar ratios comprise between about 0.2 to about 10, preferably about 0.5 to about 5, and most preferably about 0.5 to about 2.

The crosslinking reaction is run in a batch or semi continuous mode. In the latter mode, either the amine or the crosslinker is added as the initial charge and the co-reactant is then metered up for a given period of time. In one embodiment, a soluble prepolymer is first prepared by adding the entire amine monomer component and then adding continuously a fraction of the crosslinker, forming a syrup. The syrup is then emulsified as droplets in an oil continuous phase and the remaining fraction of crosslinker is added to form crosslinked beads. When the crosslinker is an alkylhalide compound, a base can be used to scavenge the acid formed during the reaction. Inorganic or organic bases are suitable. NaOH is preferred. The base to crosslinker ratio is preferably between about 0.5 to about 2.

Polymers of the invention are crosslinked materials, meaning that they do not dissolve in solvents, and, at most, swell in solvents. The ratio of swelling is expressed as the weight ratio of the swollen gel in a buffer to the dried crosslinked polymer. The ratio of swelling in physiological isotonic buffer, representative of the milieu of use, i.e. the gastrointestinal tract, is typically in the range of about 1.2 to about 100, preferably about 2 to 20.

The polymers described herein exhibit phosphate binding properties. Phosphate binding capacity is a measure of the amount of phosphate ion a phosphate binder can bind in a given solution. For example, binding capacities of phosphate binders can be measured in vitro, e.g., in water or in saline solution, or in vivo, e.g., from phosphate urinary excretion, or ex vivo, for example using aspirate liquids, e.g., chyme obtained from lab animals, patients or volunteers. Measurements can be made in a solution containing only phosphate ion, or at least no other competing solutes that compete with phosphate ions for binding to the polymer resin. In these cases, a non interfering buffer would be used. Alternatively, measurements can be made in the presence of other competing solutes, e.g., other ions or metabolites, that compete with phosphate ions (the target solute) for binding to the resin.

Phosphate binding capacity for a polymer can be calculated as $V*(C_{start}-C_{eq})/P$, expressed in mmol/gr, where V is the fixed volume of the solution used, in L; $C_{start}$ is the initial phosphate ion concentration of the solution in mM; $C_{eq}$ is the equilibrium phosphate ion concentration in the solution in mM, after a weight P, in grams, of polymer is added and equilibration allowed.

The phosphate binding capacity can range from about 0.5 mmol/gr to about 10 mmol/gr, preferably from about 2.5 mmol/gr to about 8 mmol/gr, and even more preferably from about 3 mmol/gr to about 6 mmol/gr. Several techniques are known in the art to determine the phosphate binding capacity. Examples of suitable techniques are described in the Examples section below.

Amines that may be used in the present invention are not limited to, but are typically small amines that serve as monomers or parts of monomeric units for the polymerization reactions. Examples of amines that are suitable for synthesis of the polymers of the present invention include, but are not limited to, the amines shown in Table 1.

TABLE 1

| Label | Type | Structure | MW (g/mol) |
|---|---|---|---|
| B-SM-20-TeA | Tetramine | 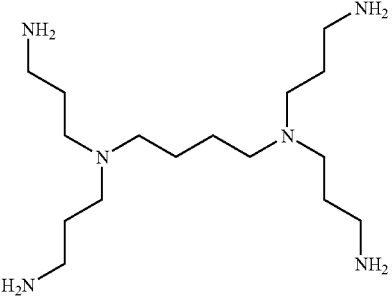 | 316.54 |
| B-SM-22-DA | Diamine | 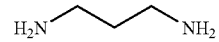 | 61.1 |
| B-SM-23-DA | Diamine | 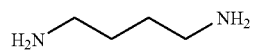 | 88.15 |
| B-SM-24-DA | Diamine | 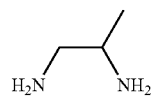 | 74.13 |
| B-SM-25-DA | Diamine | 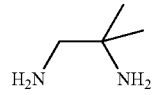 | 88.15 |
| B-SM-26-DA | Diamine | 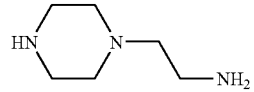 | 129.21 |
| B-SM-27-DA | Diamine | 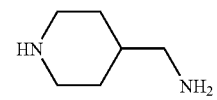 | 114.19 |
| B-SM-28-TA | Triamine | 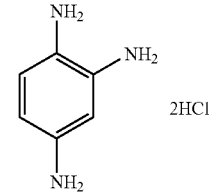 2HCl | 196.08 |
| B-SM-29-TA | Triamine | 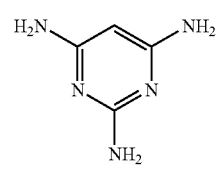 | 125.13 |

TABLE 1-continued

| Label | Type | Structure | MW (g/mol) |
|---|---|---|---|
| B-SM-31-DA | Diamine | 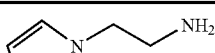 2HCl | 184.07 |
| B-SM-32-DA | Diamine | 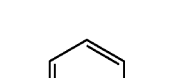 | 136.2 |

Crosslinking agents are typically compounds having at least two functional groups that are selected from a halogen group, carbonyl group, epoxy group, ester group, acid anhydride group, acid halide group, isocyanate group, vinyl group, and chloroformate group. The crosslinking agent may be attached to the carbon backbone or to the pendant nitrogen of the amine polymer. Examples of crosslinking agents that are suitable for synthesis of the polymers of the present invention include, but are not limited to, the crosslinkers shown in Table 2.

TABLE 2

| Label | Structure | Mw |
|---|---|---|
| X-EP-1 | 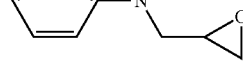 | 92.52 |
| X-EP-2 |  | 174.19 |
| X-EP-3 | 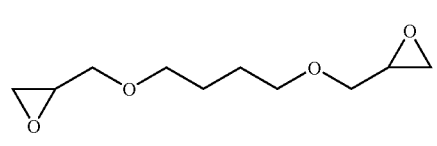 | |
| X-EP-4 | 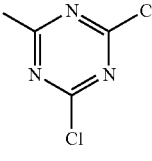 | 302.37 |
| X-EP-5 | 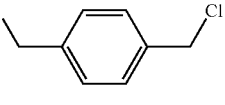 | 297.27 |
| X-EP-6 | 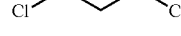 | 277.32 |
| X-EP-7 | 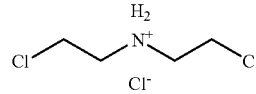 | 86.09 |
| X-EP-8 | 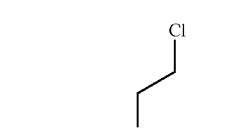 | 202.25 |
| X-CI-1 | 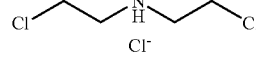 | 184.41 |
| X-CI-2 | Cl-CH2-C6H4-CH2-Cl | 175.06 |
| X-CI-3 | Cl-(CH2)3-Cl | 112.99 |
| X-CI-4 | Cl-CH2CH2-N+H2-CH2CH2-Cl Cl- | 178.49 |
| X-CI-5 | (Cl-CH2CH2)3-N+H Cl- | 240.99 |
| X-CI-6 | Cl-(CH2)4-Cl | 127.01 |

TABLE 2-continued
| Label | Structure | Mw |
|---|---|---|
| X-AC-1 | 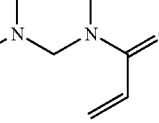 | 203.02 |
| X-AC-2 | 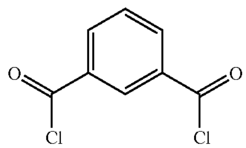 | 203.02 |
| X-AC-3 | 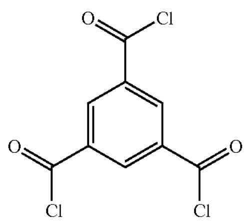 | 265.48 |
| X-AC-4 | 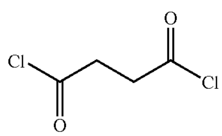 | 154.98 |
| X-AH-1 | 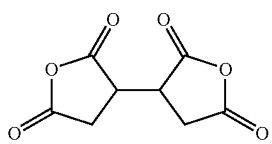 | 198.13 |
| X-AH-2 | 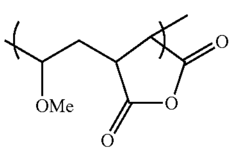 | |
| X-AH-3 | 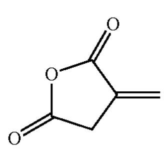 | 112.08 |
| X-Mc-1 | 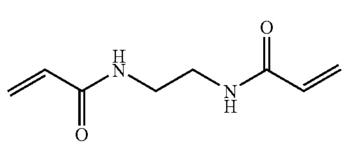 | 168.2 |
| X-Mc-2 | 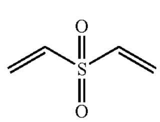 | 118.16 |
| X-Mc-3 | 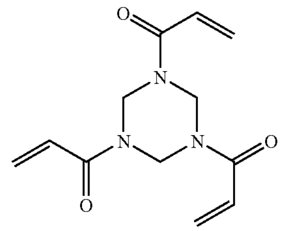 | 249.27 |
| X-Mc-4 | | 158.15 |
| X-IC-1 | OCN~~~~~NCO | 168.19 |
| X-IC-2 | 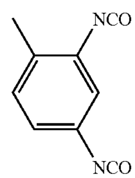 | 174.16 |
| X-IC-3 | 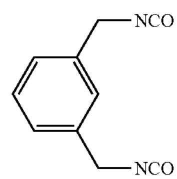 | 188.18 |
| X-IC-4 | 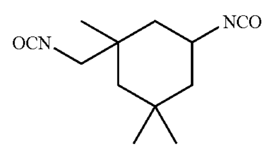 | 222.28 |
| X-ME-1 | 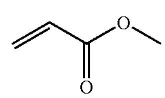 | 86.09 |
| X-ME-2 | 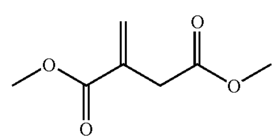 | 158.16 |
| X-ME-3 | 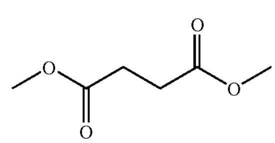 | 146.14 |
| X-ME-4 | 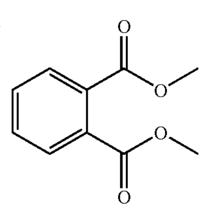 | 194.19 |

TABLE 2-continued

| Label | Structure | Mw |
|---|---|---|
| X-ME-5 | 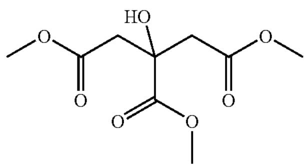 | 234.2 |
| X-ME-6 | 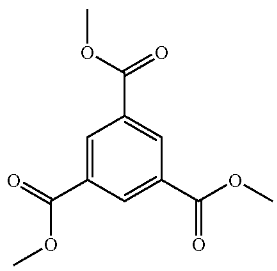 | 252.22 |
| X-ME-7 | 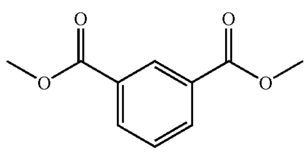 | 194.19 |
| X-ME-8 | 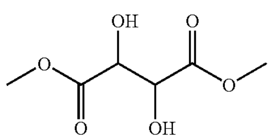 | 178.14 |
| X-ME-9 | 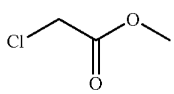 | 108.53 |

Other aspects of the invention are a crosslinked amine polymer comprising an amine of formula VI

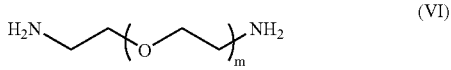

(VI)

and methods of using the same; wherein each m, independently, is equal to or greater than 3 and the amine is crosslinked with a crosslinking agent.

Treatment of Phosphate Imbalance Disorders and Renal Diseases

The term "phosphate imbalance disorder" as used herein refers to conditions in which the level of phosphorus present in the body is abnormal. One example of a phosphate imbalance disorder includes hyperphosphatemia. The term "hyperphosphatemia" as used herein refers to a condition in which the element phosphorus is present in the body at an elevated level. Typically, a patient is often diagnosed with hyperphosphatemia if the blood phosphate level is, for example, above about 4.5 milligrams per deciliter of blood and/or glomerular filtration rate is reduced to, for example, more than about 20%.

Other diseases that can be treated with the methods, compositions, and kits of the present invention include hypocalcemia, hyperparathyroidism, depressed renal synthesis of calcitriol, tetany due to hypocalcemia, renal insufficiency, and ectopic calcification in soft tissues including calcifications in joints, lungs, kidney, conjunctiva, and myocardial tissues. Also, the present invention can be used to treat ESRD and dialysis patients, including prophylactic treatment of any of the above.

Also, the polymers described herein can be used as an adjunct to other therapies e.g. those employing dietary control of phosphorus intake, dialysis inorganic metal salts and/or other polymer resins.

The compositions of the present invention are also useful in removing chloride, bicarbonate, iron ions, oxalate, and bile acids from the gastrointestinal tract. Polymers removing oxalate ions find use in the treatment of oxalate imbalance disorders, such as such as oxalosis or hyperoxaluria that increases the risk of kidney stone formation. Polymers removing chloride ions find use in treating acidosis, heartburn, acid reflux disease, sour stomach or gastritis, for example. In some embodiments, the compositions of the present invention are useful for removing fatty acids, bilirubin, and related compounds. Some embodiments may also bind and remove high molecular weight molecules like proteins, nucleic acids, vitamins or cell debris.

The present invention provides methods, pharmaceutical compositions, and kits for the treatment of animal. The term "animal" or "animal subject" as used herein includes humans as well as other mammals. One embodiment of the invention is a method of removing phosphate from the gastrointestinal tract of an animal by administering an effective amount of at least one of the crosslinked amine polymers described herein.

The term "treating" and its grammatical equivalents as used herein includes achieving a therapeutic benefit and/or a prophylactic benefit. By therapeutic benefit is meant eradication, amelioration, or prevention of the underlying disorder being treated. For example, in a hyperphosphatemia patient, therapeutic benefit includes eradication or amelioration of the underlying hyperphosphatemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of crosslinked amine polymers, described herein, to a patient suffering from renal insufficiency and/or hyperphosphatemia provides therapeutic benefit not only when the patient's serum phosphate level is decreased, but also when an improvement is observed in the patient with respect to other disorders that accompany renal failure and/or hyperphosphatemia like ectopic calcification and renal osteodistrophy. For prophylactic benefit, for example, the crosslinked amine polymers may be administered to a patient at risk of developing hyperphosphatemia or to a patient reporting one or more of the physiological symptoms of hyperphosphatemia, even though a diagnosis of hyperphosphatemia may not have been made.

The pharmaceutical compositions of the present invention include compositions wherein the crosslinked amine polymers are present in an effective amount, i.e., in an amount effective to achieve therapeutic and/or prophylactic benefit. The actual amount effective for a particular application will depend on the patient (e.g. age, weight) the condition being treated; and the route of administration. Determination of an effective amount is well within the capabilities of those skilled in the art, especially in light of the disclosure herein.

The effective amount for use in humans can be determined from animal models. For example, a dose for humans can be formulated to achieve circulating and/or gastrointestinal concentrations that have been found to be effective in animals.

The dosages of the crosslinked amine polymers in animals will depend on the disease being, treated, the route of administration, and the physical characteristics of the animal being treated. In some embodiments, the dosage levels of the crosslinked amine polymers for therapeutic and/or prophylactic uses can be from about 1 gm/day to about 30 gm/day. It is preferred that these polymers are administered along with meals. The polymers may be administered one time a day, two times a day, or three times a day. The preferred dosage range is from about 2 gm/day to about 20 gm/day and an even preferred dosage range is from about 3 gm/day to about 7 gm/day. The dose of the polymers described herein can be less than about 50 gm/day, preferably less than about 40 gm/day, more preferably less than about gm/day, even more preferably less than about 30 gm/day, even more preferred less than about 20 gm/day, and most preferred is less than about 10 gm/day.

Preferably, the crosslinked amine polymers used for therapeutic and/or prophylactic benefits can be administered alone or in the form of a pharmaceutical composition. The pharmaceutical compositions comprise the crosslinked amine polymers, one or more pharmaceutically acceptable carriers, diluents or excipients, and optionally additional therapeutic agents. For example, the crosslinked amine polymers of the present invention may be co-administered with other active pharmaceutical agents depending on the condition being treated. Examples of pharmaceutical agents that maybe co-administered include, but are not limited to, proton pump inhibitors, calcimimetics (for example, cinacalcet), Vitamin D and analogs thereof, and phosphate binders. Examples of suitable phosphate binders include, but are not limited to, aluminum carbonate, calcium carbonate, calcium acetate (PhosLo), lanthanum carbonate (Fosrenol), and Renagel. This co-administration can include simultaneous administration of the two agents in the same dosage form, simultaneous administration in separate dosage forms, and separate administration. For example, for the treatment of hyperphosphatemia, the crosslinked amine polymers may be co-administered with calcium salts which are used to treat hypoclacemia resulting from hyperphosphatemia. The calcium salt and the polymer can be formulated together in the same dosage form and administered simultaneously. Alternatively, the calcium salt and the polymer can be simultaneously administered, wherein both the agent are presenting separate formulation. In another alternative, the calcium salt can be administered just followed by the polymer, or vice versa. In the separate administration protocol, the polymer and calcium slat may be administered a few minutes apart, or a few hours apart, or a few days apart.

The polymer can be administered by injection, topically, orally, transdermally, or rectally. Preferably, the polymer or the pharmaceutical composition comprising the polymer is administered orally. The oral form in which the polymer is administered can include powder, tablet, capsule, solution, or emulsion. The effective amount can be administered in a single dose or in a series of doses separated by appropriate time intervals, such as hours.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the amines are well known in the art.

All publications and patent applications mentioned in this specification are herein incorporated by reference to the same extent as if each individual publication or patent application was specifically and individually indicated to be incorporated by reference.

It will be apparent to one of ordinary skill in the art that many changes and modification can be made to the disclosures presented herein without departing from the spirit or scope of the appended claims.

EXAMPLES

Example 1

Libraries of Crosslinked Polymers Formed in a Bulk Solution Process and Measurement for Phosphate Binding Capacity Creation of Polymer Libraries The following five examples each comprise a library comprising up to 24 crosslinked polymers. Polymers were prepared in batch reactors arranged in a 4×6 array format. Each reactor had either a 350 microliters or a 3 ml volume, was magnetically stirred, and temperature-controlled. In a typical procedure, amine, crosslinkers, solvents and optionally base were dispensed robotically in each reactor, optionally under agitation. The reactors were then sealed and heated up to the indicated temperature for 15 hours. The reactor array was then dismounted and plugs of crosslinked polymers transferred in glass vials, ground, washed repeatedly with de-ionized water, and lyophilized. The five libraries are identified below in Table 3 along with the corresponding reaction conditions used in their creation.

TABLE 3

| Example | Library identification | Reaction temperature (° C.) | Reactor volume (microliters) |
|---|---|---|---|
| 1 | 100275 | 85 | 350 |
| 2 | 100277 | 60 | 350 |
| 3 | 100279 | 80 | 350 |
| 4 | 100353 | 80 | 350 |
| 5 | 100384 | 80 | 3000 |

Phosphate Binding Capacity Measurements in a Non Interfering Buffer

Binding capacities for phosphate ion were also determined for each of the polymers of the libraries. An aliquot of dried resin of weight P(gr), was mixed under gentle agitation with a fixed volume, V(L), of a phosphate ion solution of concentration $C_{start}$(mM) buffered at pH 6.5. The solution can be referred to as a non-interfering buffer as it contains no other competing solutes that compete with the phosphate ions for binding to the polymer resin. After resin equilibration, the solution was decanted by centrifugation and the supernatant analyzed for residual phosphate concentration by ionic chromatography, $C_{eq}$(mM). The binding capacity was calculated as $V*(C_{start}-C_{eq})/P$, expressed in mmol/gr as indicated in the tables for the corresponding polymers.

Results

Tables 4-8 provide materials and the quantities used in forming the polymers of each of the 5 libraries, along with the measured phosphate binding capacities in a non interfering buffer for the polymers formed. Entries correspond to the weight of chemicals used in each reaction well in mg, along with the phosphate binding capacity of the polymer gel obtained (blank indicates no crosslinked gel was formed in that particular reaction).

TABLE 4

Library: Plate3 (ID: 100275) Unit: mg

| Row | Col | water | B-SM-22-DA | X-CI-3 | NaOH | DMSO | Phosphate binding (mmol/gr) |
|---|---|---|---|---|---|---|---|
| 1 | 1 | 128.51 | 67.74 | 51.63 | 9.14 | 0.00 | |
| 1 | 2 | 130.70 | 57.94 | 61.82 | 10.94 | 0.00 | |
| 1 | 3 | 132.33 | 50.61 | 69.43 | 12.29 | 0.00 | |
| 1 | 4 | 133.59 | 44.93 | 75.33 | 13.33 | 0.00 | 3.042 |
| 1 | 5 | 134.60 | 40.39 | 80.04 | 14.17 | 0.00 | 0 |
| 1 | 6 | 135.43 | 36.69 | 83.89 | 14.85 | 0.00 | 0 |
| 2 | 1 | 136.42 | 32.26 | 88.50 | 15.66 | 0.00 | 3.703 |
| 2 | 2 | 137.05 | 29.41 | 91.45 | 16.19 | 0.00 | 3.624 |
| 2 | 3 | 137.58 | 27.03 | 93.93 | 16.63 | 0.00 | 2.858 |
| 2 | 4 | 138.03 | 25.00 | 96.03 | 17.00 | 0.00 | 2.566 |
| 2 | 5 | 138.42 | 23.26 | 97.84 | 17.32 | 0.00 | 2.761 |
| 2 | 6 | 138.76 | 21.74 | 99.42 | 17.60 | 0.00 | 2.82 |
| 3 | 1 | 132.04 | 64.98 | 49.52 | 17.53 | 34.60 | |
| 3 | 2 | 134.77 | 55.13 | 58.82 | 20.82 | 47.26 | |
| 3 | 3 | 136.79 | 47.87 | 65.67 | 23.25 | 57.22 | |
| 3 | 4 | 138.34 | 42.30 | 70.93 | 25.11 | 65.27 | 3.087 |
| 3 | 5 | 139.57 | 37.90 | 75.09 | 26.58 | 71.91 | 2.946 |
| 3 | 6 | 140.56 | 34.32 | 78.47 | 27.78 | 77.48 | 2.535 |
| 4 | 1 | 141.75 | 30.06 | 82.48 | 29.20 | 79.73 | 2.674 |
| 4 | 2 | 142.50 | 27.35 | 85.04 | 30.11 | 90.45 | 3.038 |
| 4 | 3 | 143.13 | 25.09 | 87.18 | 30.86 | 97.98 | 2.895 |
| 4 | 4 | 143.66 | 23.17 | 88.99 | 31.50 | 103.56 | 2.571 |
| 4 | 5 | 144.12 | 21.52 | 90.54 | 32.05 | 107.86 | 2.636 |
| 4 | 6 | 0.00 | 0.00 | 0.00 | 0.00 | 0.00 | 5.374 |

TABLE 5

Library: Plate1 (ID: 100277) Unit: mg

| Row | Col | water | B-SM-20-TeA | X-EP-1 | X-EP-4 | DMF | Phosphate binding (mmol/gr) |
|---|---|---|---|---|---|---|---|
| 1 | 1 | 123.69 | 110.75 | 12.95 | 0.00 | | |
| 1 | 2 | 124.02 | 107.66 | 16.36 | 0.00 | 0.00 | |
| 1 | 3 | 124.33 | 104.74 | 19.59 | 0.00 | 0.00 | |
| 1 | 4 | 124.63 | 101.98 | 22.65 | 0.00 | 0.00 | |
| 1 | 5 | 124.91 | 99.35 | 25.55 | 0.00 | 0.00 | 4.183 |
| 1 | 6 | 125.17 | 96.86 | 28.31 | 0.00 | 0.00 | 4.237 |
| 2 | 1 | 125.59 | 92.98 | 32.61 | 0.00 | 0.00 | 4.631 |
| 2 | 2 | 125.89 | 90.08 | 35.81 | 0.00 | 0.00 | 4.594 |
| 2 | 3 | 126.18 | 87.37 | 38.81 | 0.00 | 0.00 | 4.667 |
| 2 | 4 | 126.45 | 84.81 | 41.64 | 0.00 | 0.00 | 4.586 |
| 2 | 5 | 126.71 | 82.40 | 44.31 | 0.00 | 0.00 | 4.535 |
| 2 | 6 | 126.95 | 80.12 | 46.83 | 0.00 | 0.00 | 4.311 |
| 3 | 1 | 0.00 | 181.12 | 0.00 | 34.60 | 0.00 | |
| 3 | 2 | 0.00 | 159.58 | 0.00 | 47.26 | 104.77 | |
| 3 | 3 | 0.00 | 142.63 | 0.00 | 57.22 | 118.23 | 3.112 |
| 3 | 4 | 0.00 | 128.93 | 0.00 | 65.27 | 128.56 | 2.991 |
| 3 | 5 | 0.00 | 117.63 | 0.00 | 71.91 | 136.73 | 2.798 |
| 3 | 6 | 0.00 | 108.15 | 0.00 | 77.48 | 143.35 | 3.271 |
| 4 | 1 | 0.00 | 104.33 | 0.00 | 79.73 | 148.83 | 3.258 |
| 4 | 2 | 0.00 | 86.08 | 0.00 | 90.45 | 156.12 | 3.062 |
| 4 | 3 | 0.00 | 73.27 | 0.00 | 97.98 | 160.76 | 2.176 |
| 4 | 4 | 0.00 | 63.77 | 0.00 | 103.56 | 164.62 | 2.228 |
| 4 | 5 | 0.00 | 56.46 | 0.00 | 107.86 | 167.88 | 2.407 |
| 4 | 6 | 0.00 | 0.00 | 0.00 | 0.00 | 170.67 | 5.224 |
| 4 | 6 | 0.00 | 0.00 | 0.00 | 0.00 | 0.00 | |

TABLE 6

Library: Plate3 (ID: 100279) Unit: mg

| Row | Col | water | B-SM-20-TeA | X-CI-3 | X-CI-2 | Phosphate binding (mmol/gr) |
|---|---|---|---|---|---|---|
| 1 | 1 | 123.95 | 108.47 | 15.49 | 0.00 | |
| 1 | 2 | 124.34 | 104.88 | 19.47 | 0.00 | |
| 1 | 3 | 124.70 | 101.51 | 23.19 | 0.00 | |
| 1 | 4 | 125.04 | 98.36 | 26.68 | 0.00 | |
| 1 | 5 | 125.36 | 95.40 | 29.97 | 0.00 | 3.958 |
| 1 | 6 | 125.66 | 92.61 | 33.06 | 0.00 | 4.309 |
| 2 | 1 | 126.13 | 88.30 | 37.82 | 0.00 | 4.417 |
| 2 | 2 | 126.47 | 85.14 | 41.33 | 0.00 | 4.424 |
| 2 | 3 | 126.78 | 82.19 | 44.59 | 0.00 | 4.392 |
| 2 | 4 | 127.08 | 79.44 | 47.64 | 0.00 | 4.407 |
| 2 | 5 | 127.36 | 76.87 | 50.49 | 0.00 | 4.14 |
| 2 | 6 | 127.62 | 74.46 | 53.16 | 0.00 | 4.314 |
| 3 | 1 | 0.00 | 118.41 | 0.00 | 26.19 | |
| 3 | 2 | 0.00 | 102.78 | 0.00 | 29.56 | |
| 3 | 3 | 0.00 | 90.80 | 0.00 | 32.14 | |
| 3 | 4 | 0.00 | 81.32 | 0.00 | 34.18 | |
| 3 | 5 | 0.00 | 73.64 | 0.00 | 35.84 | |
| 3 | 6 | 0.00 | 67.28 | 0.00 | 37.21 | 2.237 |
| 4 | 1 | 0.00 | 58.81 | 0.00 | 39.03 | 2.403 |
| 4 | 2 | 0.00 | 53.43 | 0.00 | 40.19 | 2.704 |
| 4 | 3 | 0.00 | 48.96 | 0.00 | 41.15 | 2.614 |
| 4 | 4 | 0.00 | 45.17 | 0.00 | 41.97 | 1.714 |
| 4 | 5 | 0.00 | 41.93 | 0.00 | 42.67 | 2.294 |
| 4 | 6 | 0.00 | 0.00 | 0.00 | 0.00 | 5.295 |

TABLE 7

Library: Plate1 (ID: 100353) Unit: mg

| Row | Col | B-SM-20-TeA | 22-DA | X-CI-3 | NaOH | Phosphate binding (mmol/gr) |
|---|---|---|---|---|---|---|
| 1 | 1 | 142.77 | 11.14 | 33.97 | 24.05 | |
| 1 | 2 | 117.71 | 9.19 | 44.82 | 31.73 | |
| 1 | 3 | 100.13 | 7.82 | 52.42 | 37.12 | 5.838 |
| 1 | 4 | 87.12 | 6.80 | 58.05 | 41.10 | 5.38 |
| 1 | 5 | 77.10 | 6.02 | 62.39 | 44.17 | 5.549 |
| 1 | 6 | 69.15 | 5.40 | 65.83 | 46.61 | 5.826 |
| 2 | 1 | 64.71 | 5.05 | 67.75 | 47.97 | 5.452 |
| 2 | 2 | 57.99 | 4.53 | 70.66 | 50.03 | 3.358 |
| 2 | 3 | 52.54 | 4.10 | 73.01 | 51.70 | 3.45 |
| 2 | 4 | 48.02 | 3.75 | 74.97 | 53.08 | 4.27 |
| 2 | 5 | 44.22 | 3.45 | 76.61 | 54.24 | 3.469 |
| 2 | 6 | 40.98 | 3.20 | 78.02 | 55.24 | 4.058 |
| 3 | 1 | 111.71 | 26.16 | 39.87 | 28.23 | |
| 3 | 2 | 89.37 | 20.93 | 51.04 | 36.14 | |
| 3 | 3 | 74.48 | 17.44 | 58.49 | 41.41 | 5.154 |
| 3 | 4 | 63.85 | 14.95 | 63.81 | 45.18 | 5.784 |
| 3 | 5 | 55.87 | 13.08 | 67.80 | 48.01 | 5.596 |
| 3 | 6 | 49.66 | 11.63 | 70.91 | 50.20 | 5.287 |
| 4 | 1 | 46.24 | 10.83 | 72.62 | 51.42 | 5.261 |
| 4 | 2 | 41.13 | 9.63 | 75.17 | 53.23 | 4.743 |
| 4 | 3 | 37.04 | 8.67 | 77.22 | 54.67 | 4.076 |
| 4 | 4 | 33.69 | 7.89 | 78.90 | 55.86 | 3.924 |
| 4 | 5 | 30.90 | 7.24 | 80.29 | 56.85 | 2.896 |
| 4 | 6 | 0.00 | 0.00 | 0.00 | 0.00 | 5.287 |

TABLE 8

Library: Plate1 (ID: 100384) Unit: mg

| Row | Col | X-CI-3 | B-SM-22-DA | water | NaOH | Phosphate binding (mmol/gr) |
|---|---|---|---|---|---|---|
| 1 | 1 | 643.88 | 422.44 | 1752.36 | 227.94 | |
| 1 | 2 | 692.40 | 378.56 | 1743.80 | 245.12 | 4.362 |
| 1 | 3 | 731.79 | 342.94 | 1736.85 | 259.06 | 4.09 |
| 1 | 4 | 764.40 | 313.44 | 1731.10 | 270.61 | 3.198 |

TABLE 8-continued

Library: Plate1 (ID: 100384) Unit: mg

| Row | Col | X-Cl-3 | B-SM-22-DA | water | NaOH | Phosphate binding (mmol/gr) |
|---|---|---|---|---|---|---|
| 1 | 5 | 791.85 | 288.62 | 1726.26 | 280.33 | 2.951 |
| 1 | 6 | 815.27 | 267.44 | 1722.12 | 288.62 | 2.005 |
| 2 | 1 | 643.88 | 422.44 | 1752.36 | 227.94 | |
| 2 | 2 | 692.40 | 378.56 | 1743.80 | 245.12 | |
| 2 | 3 | 731.79 | 342.94 | 1736.85 | 259.06 | |
| 2 | 4 | 764.40 | 313.44 | 1731.10 | 270.61 | 4.794 |
| 2 | 5 | 791.85 | 288.62 | 1726.26 | 280.33 | |
| 2 | 6 | 815.27 | 267.44 | 1722.12 | 288.62 | 4.332 |
| 3 | 1 | 643.88 | 422.44 | 1752.36 | 227.94 | |
| 3 | 2 | 692.40 | 378.56 | 1743.80 | 245.12 | |
| 3 | 3 | 731.79 | 342.94 | 1736.85 | 259.06 | |
| 3 | 4 | 764.40 | 313.44 | 1731.10 | 270.61 | 4.511 |
| 3 | 5 | 791.85 | 288.62 | 1726.26 | 280.33 | 5.086 |
| 3 | 6 | 815.27 | 267.44 | 1722.12 | 288.62 | 4.61 |
| 4 | 1 | 643.88 | 422.44 | 1752.36 | 227.94 | |
| 4 | 2 | 692.40 | 378.56 | 1743.80 | 245.12 | |
| 4 | 3 | 731.79 | 342.94 | 1736.85 | 259.06 | |
| 4 | 4 | 764.40 | 313.44 | 1731.10 | 270.61 | |
| 4 | 5 | 791.85 | 288.62 | 1726.26 | 280.33 | 4.816 |
| 4 | 6 | 0.00 | 0.00 | 0.00 | 0.00 | 5.17 |

Example 2

Synthesis of 1,3-Diaminopropane/epichlorohydrin Crosslinked Beads Formed in a Suspension Process A 3-liter reaction vessel was used, comprising a three necked round bottom flask with four side baffles. The reaction flask was equipped with an oil heating bath, cold-water reflux condenser, and mechanical stirrer with a 3 inch propeller. To this reaction vessel was introduced a solution of 1,3-diaminopropane (90.2 g, 1.21 mole) dissolved in 90.2 g of water, surfactant (branched dodecylbenzene sulfonic acid sodium salt, 6.4 g dissolved in 100 g of water) and 1 Kg of toluene. This initial charge was agitated to 600 rpm for 2 minutes and then lowered to 300 rpm for 10 minutes before the epichlorohydrin was added. The 300 rpm speed was maintained through out the remainder of the experiment. The solution was heated to 80° C. and also maintained at this temperature through out the experiment.

In a separate vessel, a 40 mass % solution of epichlorohydrin in toluene was prepared. Using a syringe pump, 1.2 equivalents of epichlorohydrin (134.7 g, (1.45 mole)) were added to the initial charge reaction vessel over a 3 hour period. The reaction was continued for an additional 2 hours before adding 0.75 equivalents of sodium hydroxide (36.5 g (0.91 mole)) in a 40 weight % solution. The sodium hydroxide solution was added to the reaction via a syringe pump over a 2.5 hour period. The reaction was maintained at 80° C. for a further 8 hours.

After this time, beads that formed were purified by removing the toluene, washing with 1000 ml of acetone, followed by methanol, a 20% solution of NaOH (to remove the surfactant), and then twice more with deionized water. The beads were freeze dried for 3 days to give a fine white powder weighing at 160 g (92% yield) and having a mean diameter of 93 μm.

Example 3

Synthesis of 1,3-Diaminopropane/1,3-Dichloropropane Crosslinked Polymer

Using water as solvent, 1000 mg of B-SM-22-DA was mixed with 1524 mg of X—Cl-3 and 2524 mg of water in a 20 mL scintillation vial. The reaction was subjected to magnetic stirring and maintained at a temperature of 80° C. overnight, followed by a temperature of 90° C. for two additional hours. A 34 wt. % of reaction mixture (1716 mg) was purified by 3 washing in water/centrifugation steps and gave 144.7 mg of powder of the polymer of the present example.

Example 4

Synthesis of 1,3-Diaminopropane/1,3-Dichloropropane Crosslinked Polymer

Using water as a solvent, 2000 mg of B-SM-22-DA was mixed with 3048 mg of X—Cl-3 and 5048 mg of water in a 20 mL scintillation vial. The reaction was subjected to magnetic stirring and maintained at a temperature of 80° C. overnight.

3597 mg of NaOH solution at 30 wt. % in water was added after 3 hours of reaction to scavenge the acid formed during the reaction as the crosslinker used was an alkylhalide. A 20.3 wt. % of reaction mixture (2773.5 mg) was purified by 3 washing in water/centrifugation steps and gave 591.3 mg of powder of the polymer of the present example.

Example 5

Synthesis of Crosslinked Beads Prepared with 1,3-Diaminopropane/1,3-dichloropropane Using a Prepolymer Approach Preparation of Pre-Polymer The reaction vessel used was a 250 mL, two necked round bottom flask, equipped with a cold-water reflux condenser, magnetic stirrer, and run over an argon atmosphere. To this reaction vessel is introduced a solution of 1,3-diaminopropane (31.15 g, 0.42 mole) dissolved in 30.15 g of water. This initial charge is agitated to 300 rpm. The solution was heated to 80° C. and maintained at this temperature through out the experiment. Using a syringe pump, 1 equivalent (47.47 g, 40.0 mL, 0.42 mol) of 1,3 dichloropropane (Aldrich 99%) was added over a 2-hour period. The reaction was continued for an additional 2 hours before adding 10 mole % (with respect to 1,3-diaminopropane) of sodium hydroxide (1.68 g (0.042 mole) of NaOH and made up to a 40 weight % solution of water). The sodium hydroxide solution was added to the reaction via pipette over a 2 minute period. The reaction was maintained at 80° C. for a further 4 hours. The solution at 80° C. is viscous and upon cooling to 25° C. becomes a solid plug that is readily soluble in water.

Purification

To the solid plug water is added, washing with 200 ml of water and 200 mL of MeOH. This is then added to a 1 L beaker that contains a 50/50 solution of MeOH/Isopropyl alcohol. The white polymer precipitates. After placing the suspension into a centrifuge, the supernatant liquid is removed. This process is repeated using isopropyl alcohol a further 2 times. The white precipitate is then dried under reduced pressure at room temperature to remove the isopropyl alcohol. Weight of polymer isolated: Mn (GPC relative to polyethylenimine standard) ~600.

Synthesis Crosslinked Particles

The white pre-polymer (8.7 g) was placed into a flask with 1.3 g of branched dodecylbenzene sulfonic acid sodium salt (30 wgt % solution in water) and 34.8 g of toluene. This gave a 20 weight % solution of polymer suspended in toluene. The polymer was ground to micron sized particles with a mechanical grinder (Brand: IKA. Model: Ultra-Turax T8). 2.2 g of the resulting suspension was loaded into a 10 mL reaction flask equipped with a heater, a mechanical stirrer, and a syringe pump. The reaction flask was charged with an additional 3779 mg of toluene. The flask was heated to 80° C. and the stirrer was turned on (500 RPM). After 3 hours of stirring at this temperature, 112.2 mg (0.0012 mole) of epichlorohydrin was added over a 1.5-hour period. The reaction was allowed to proceed a further 2 hours before the addition of 224.4 mg (0.0056 mol) of sodium hydroxide (in a 40 weight % solution of water), which was delivered over a 2 hour period. The reaction was allowed to cool to room temperature and the stirring was stopped. The beads were purified by removing the toluene, washing with methanol, and then a 20% solution of NaOH (to remove the surfactant) and twice more with deionized water. The beads were freeze dried for 3 days to give a fine white powder. The binding capacity measured in a non interfering buffer was 3.85 mmol/gr.

Example 6

Binding Capacity in a Digestion Model

This procedure was designed to mimic the conditions of use of a phosphate binding polymer in a GI tract and measure the binding characteristics of the polymer for phosphate (target solute) in the presence of other metabolites (competing solutes). A liquid meal was prepared and the polymers of each of Examples 2, 3, or 4 were added to the meal composition and the meal was artificially digested in the presence of pepsin and pancreatic juice. The sequence of addition of enzymes and the pH profile were controlled so that the digestion process was simulated down to the jejunum level. An aliquot of the digested meal mimic was centrifuged and the supernatant assayed for phosphate. The phosphate binding assay was like the one described above with non-interfering buffer, except that liquid of the meal digest mimic was used. The binding capacity in the meal digest was calculated as indicated above and results are reported in Table 9 below.

TABLE 9

| | Phosphate binding in a non interfering buffer | | | Phosphate binding in a meal digest | | |
|---|---|---|---|---|---|---|
| Example | $C_{start}$(mM) | $C_{eq}$(mM) | Capacity (mmol/gr) | $C_{start}$(mM) | $C_{eq}$(mM) | Capacity (mmol/gr) |
| 2 | 20.1 | 10.56 | 3.81 | 8.01 | 5.31 | 1.08 |
| 3 | 20.1 | 12.27 | 3.13 | 8.01 | 5.83 | 0.74 |
| 4 | 20.1 | 9.32 | 4.31 | 8.01 | 3.87 | 1.66 |

Example 7

Binding Capacity in Ex-vivo Aspirates

Using a tube placed in the lumen of the small intestine, healthy patients are given a meal of the same composition as the one prepared for the digestion mimic in Example 6 and aliquots of chyme are then sampled.

Subjects are intubated with a double lumen polyvinyl tube with a mercury-weighted bag attached to the end of the tube to facilitate movement of the tube into the small intestine. Using fluoroscopy to direct placement, one aspiration aperture of the double lumen tube is located in the stomach, and the other aperture is at the Ligament of Treitz (in the upper jejunum).

After correct tube placement, 550 mL of the liquefied test meal (supplemented with a marker, polyethylene glycol (PEG) –2 g/550 mL) is infused into the stomach through the gastric aperture at a rate of 22 mL per minute. It requires approximately 25 minutes for the entire meal to reach the stomach, simulating the duration of time required to eat normal meals.

Jejunal chyme is aspirated from the tube whose lumen is located at the Ligament of Treitz. This fluid is collected continuously during 30 minute intervals for a two and a half hour period. This results in 5 specimens that are mixed, measured for volume, and lyophilized.

A phosphate binding assay can be carried out on the ex-vivo aspirates. The phosphate binding procedure can be like the one described above with non-interfering buffer, except that the ex-vivo aspirate liquid is used (after reconstitution of the freeze-dried material in the proper amount of de-ionized water). The phosphate binding capacities in the ex-vivo aspirate can be calculated in the same way and are expected to be similar to those reported with the meal mimic experiments.

What is claimed is:

1. A polymeric composition comprising a crosslinked amine polymer, wherein said polymer comprises a crosslinked amine, said amine being at least one of

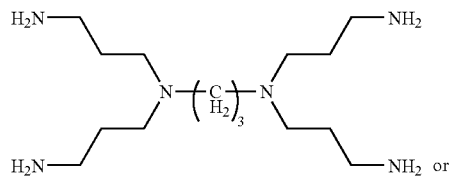

-continued

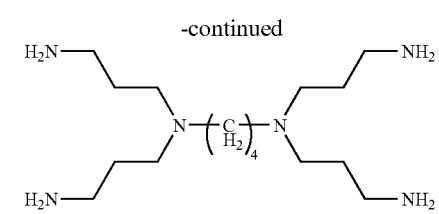

and said amine being crosslinked with a crosslinking agent.

2. A polymeric composition comprising a crosslinked amine polymer, the polymer comprising a crosslinked amine,

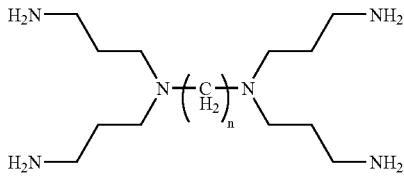

wherein n is 3, 4 or 5, and the amine is crosslinked with a crosslinking agent.

3. The polymeric composition of claim 2 wherein n is 3.

4. The polymeric composition of claim 2 wherein n is 5.

5. A polymeric composition comprising a crosslinked amine polymer, the polymer comprising a crosslinked amine,

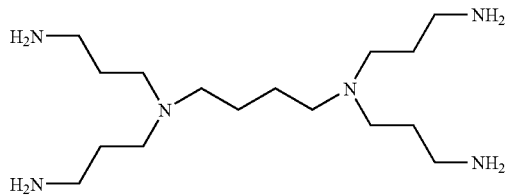

wherein the amine is crosslinked with a crosslinking agent.

6. The polymeric composition of claim 1 wherein the crosslinking agent is a compound having at least two functional groups, each functional group being selected from halogen, carbonyl, epoxy, ester, acid anhydride, acid halide, isocyanate, vinyl, and chloroformate.

7. The polymeric composition of claim 1 wherein the crosslinking agent is epichlorohydrin.

8. The polymeric composition of claim 1 wherein the molar ratio of crosslinking agent to amine ranges from about 0.2 to about 10.

9. The polymeric composition of claim 1 wherein the molar ratio of crosslinking agent to amine ranges from about 0.5 to about 5.

10. The polymeric composition of claim 1 wherein the crosslinked amine polymer is insoluble in a physiological isotonic buffer.

11. The polymeric composition of claim 1 wherein the crosslinked amine polymer has a swelling ratio in physiological isotonic buffer ranging from about 1.2 to about 100.

12. The polymeric composition of claim 1 wherein the crosslinked amine polymer has a swelling ratio in physiological isotonic buffer ranging from about 2 to 20.

13. The polymeric composition of claim 1 wherein the crosslinked amine polymer has a phosphate binding capacity in a non-interfering buffer ranging from about 0.5 mmol/g to about 10 mmol/g.

14. The polymeric composition of claim 1 wherein the crosslinked amine polymer has a phosphate binding capacity in a non-interfering buffer ranging from about 2.5 mmol/g to about 8 mmol/g.

15. The polymeric composition of claim 1 wherein the crosslinked amine polymer has a phosphate binding capacity in a non-interfering buffer ranging from about 3 mmol/g to about 6 mmol/g.

16. The polymeric composition of claim 1 wherein the polymer is a copolymer comprising several different amines as crosslinked amine moieties.

17. The polymeric composition of claim 1 wherein the polymer is a copolymer further comprising a diamine, a triamine or a tetramine as crosslinked amine moieties.

18. The polymeric composition of claim 1 wherein the polymer is a copolymer further comprising a diamine as crosslinked amine moieties.

19. The polymeric composition of claim 1 wherein the polymer is a copolymer further comprising 1,3-diaminopropane as crosslinked amine moieties.

20. The polymeric composition of claim 5 wherein the crosslinking agent is epichlorohydrin, the molar ratio of crosslinking agent to amine ranges from about 0.2 to about 5, the polymer is insoluble in a physiological isotonic buffer, the polymer has a swelling ratio in physiological isotonic buffer ranging from about 2 to 20, and the polymer has a binding capacity in a non-interfering buffer ranging from about 2.5 mmol/g to about 8 mmol/g.

21. A polymeric composition comprising a crosslinked amine polymer in bead form, the polymer comprising repeat units derived from polymerization of an amine and a crosslinking agent, the amine having the formula

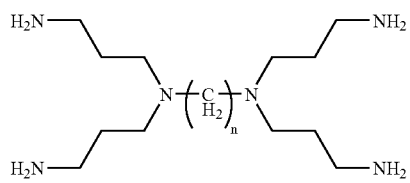

wherein n is 3, 4 or 5.

22. The polymeric composition of claim 21 wherein the polymer has a phosphate binding capacity in a non-interfering buffer ranging from about 0.5 mmol/g to about 10 mmol/g.

23. The polymeric composition of claim 21 wherein the molar ratio of crosslinking agent to amine ranges from about 0.2 to about 10, the polymer is insoluble in a physiological isotonic buffer, the polymer has a swelling ratio in physiological isotonic buffer ranging from about 2 to 20, and the polymer has a phosphate binding capacity in a non-interfering buffer ranging from about 0.5 mmol/g to about 10 mmol/g.

24. The polymeric composition of claim 21 wherein n is 3.

25. The polymeric composition of claim 21 wherein n is 4.

26. The polymeric composition of claim 21 wherein n is 5.

27. The polymeric composition of claim 22 wherein n is 3.

28. The polymeric composition of claim 22 wherein n is 4.

29. The polymeric composition of claim 22 wherein n is 5.

30. The polymeric composition of claim 23 wherein n is 3.

31. The polymeric composition of claim 23 wherein n is 4.

32. The polymeric composition of claim 23 wherein n is 5.

33. The polymeric composition as recited in claim 2 wherein said crosslinking agent is 1,3-dichloropropane or epichlorohydrin.

34. The polymeric composition of claim 2 wherein the crosslinking agent is epichlorohydrin.

35. The polymeric composition of claim 2 wherein the molar ratio of crosslinking agent to amine ranges from about 0.2 to about 10.

36. The polymeric composition of claim 2 wherein the molar ratio of crosslinking agent to amine ranges from about 0.5 to about 5.

37. The polymeric composition of claim 2 wherein the crosslinked amine polymer is insoluble in a physiological isotonic buffer.

38. The polymeric composition of claim 2 wherein the crosslinking agent is a compound having at least two functional groups, each functional group being selected from halogen, carbonyl, epoxy, ester, acid anhydride, acid halide, isocyanate, vinyl, and chloroformate.

39. The polymeric composition of claim 2 wherein the crosslinked amine polymer has a swelling ratio in physiological isotonic buffer ranging from about 1.2 to about 100.

40. The polymeric composition of claim 2 wherein the crosslinked amine polymer has a swelling ratio in physiological isotonic buffer ranging from about 2 to 20.

41. The polymeric composition of claim 2 wherein the crosslinked amine polymer has a phosphate binding capacity in a non-interfering buffer ranging from about 0.5 mmol/g to about 10 mmol/g.

42. The polymeric composition of claim 2 wherein the crosslinked amine polymer has a phosphate binding capacity in a non-interfering buffer ranging from about 2.5 mmol/g to about 8 mmol/g.

43. The polymeric composition of claim 2 wherein the crosslinked amine polymer has a phosphate binding capacity in a non-interfering buffer ranging from about 3 mmol/g to about 6 mmol/g.

44. The polymeric composition of claim 2 wherein the polymer is a copolymer comprising several different amines as crosslinked amine moieties.

45. The polymeric composition of claim 2 wherein the polymer is a copolymer further comprising a diamine, a triamine or a tetramine as crosslinked amine moieties.

46. The polymeric composition of claim 2 wherein the polymer is a copolymer further comprising a diamine as crosslinked amine moieties.

47. The polymeric composition of claim 2 wherein the polymer is a copolymer further comprising 1,3-diaminopropane as crosslinked amine moieties.

48. The polymeric composition as recited in claim 5 wherein said crosslinking agent is 1,3-dichloropropane or epichlorohydrin.

49. The polymeric composition of claim 5 wherein the crosslinking agent is a compound having at least two functional groups, each functional group being selected from halogen, carbonyl, epoxy, ester, acid anhydride, acid halide, isocyanate, vinyl, and chloroformate.

50. The polymeric composition of claim 5 wherein the crosslinking agent is epichlorohydrin.

51. The polymeric composition of claim 5 wherein the molar ratio of crosslinking agent to amine ranges from about 0.2 to about 10.

52. The polymeric composition of claim 5 wherein the molar ratio of crosslinking agent to amine ranges from about 0.5 to about 5.

53. The polymeric composition of claim 5 wherein the crosslinked amine polymer is insoluble in a physiological isotonic buffer.

54. The polymeric composition of claim 5 wherein the crosslinked amine polymer has a swelling ratio in physiological isotonic buffer ranging from about 1.2 to about 100.

55. The polymeric composition of claim 5 wherein the crosslinked amine polymer has a swelling ratio in physiological isotonic buffer ranging from about 2 to 20.

56. The polymeric composition of claim 5 wherein the crosslinked amine polymer has a phosphate binding capacity in a non-interfering buffer ranging from about 0.5 mmol/g to about 10 mmol/g.

57. The polymeric composition of claim 5 wherein the crosslinked amine polymer has a phosphate binding capacity in a non-interfering buffer ranging from about 2.5 mmol/g to about 8 mmol/g.

58. The polymeric composition of claim 5 wherein the crosslinked amine polymer has a phosphate binding capacity in a non-interfering buffer ranging from about 3 mmol/g to about 6 mmol/g.

59. The polymeric composition of claim 5 wherein the polymer is a copolymer comprising several different amines as crosslinked amine moieties.

60. The polymeric composition of claim 5 wherein the polymer is a copolymer further comprising a diamine, a triamine or a tetramine as crosslinked amine moieties.

61. The polymeric composition of claim 5 wherein the polymer is a copolymer further comprising a diamine as crosslinked amine moieties.

62. The polymeric composition of claim 5 wherein the polymer is a copolymer further comprising 1,3-diaminopropane as crosslinked amine moieties.

63. The polymeric composition of claim 2 wherein the polymeric composition consists essentially of the polymerization product of the amine corresponding to the structure

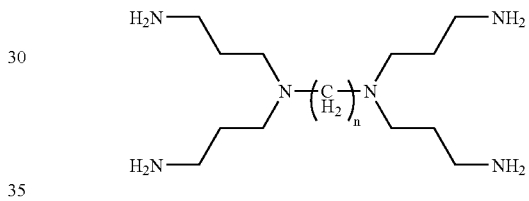

and a crosslinking agent, wherein n is 3, 4, or 5.

64. The polymeric composition of claim 63 wherein the crosslinking agent is epichlorohydrin.

65. The polymeric composition of claim 63 wherein the crosslinking agent is 1,3-dichloropropane.

66. The polymeric composition of claim 63 wherein the polymeric composition consists essentially of the polymerization product derived from crosslinking the amine with the crosslinking agent using a molar ratio of crosslinking agent to amine ranging from about 0.5 to about 5.

67. The polymeric composition of claim 2 wherein the polymeric composition consists essentially of the polymerization product of the amine corresponding to the structure

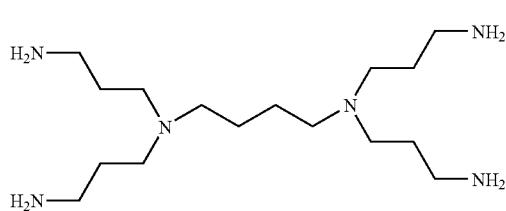

and a crosslinking agent, the crosslinking agent being epichlorohydrin.

68. The polymeric composition as recited in claim 1 wherein said crosslinking agent is 1,3-dichloropropane or epichlorohydrin.

* * * * *